(12) United States Patent
Dyer

(10) Patent No.: US 12,263,070 B2
(45) Date of Patent: Apr. 1, 2025

(54) LOW RISE PROTECTIVE UNDERWEAR AND METHOD OF FORMING THE SAME

(71) Applicant: FIRST QUALITY PRODUCTS, INC., Great Neck, NY (US)

(72) Inventor: Brian K. Dyer, Gray, GA (US)

(73) Assignee: FIRST QUALITY PRODUCTS, INC., Great Neck, NY (US)

( * ) Notice: Subject to any disclaimer, the term of this patent is extended or adjusted under 35 U.S.C. 154(b) by 0 days.

(21) Appl. No.: 17/569,627

(22) Filed: Jan. 6, 2022

(65) Prior Publication Data

US 2022/0211552 A1 Jul. 7, 2022

Related U.S. Application Data

(60) Provisional application No. 63/134,701, filed on Jan. 7, 2021.

(51) Int. Cl.
| | |
|---|---|
| *A61F 13/15* | (2006.01) |
| *A61F 13/49* | (2006.01) |
| *A61F 13/496* | (2006.01) |

(52) U.S. Cl.
CPC ...... *A61F 13/496* (2013.01); *A61F 13/15593* (2013.01); *A61F 13/49015* (2013.01); *A61F 2013/49098* (2013.01)

(58) Field of Classification Search
None
See application file for complete search history.

(56) References Cited

U.S. PATENT DOCUMENTS

2005/0224171 A1\* 10/2005 Hoshika ............ A61F 13/15804
156/301

FOREIGN PATENT DOCUMENTS

WO WO-2017203955 A1 \* 11/2017 ........... A61F 13/494

\* cited by examiner

*Primary Examiner* — Chinyere J Rushing-Tucker
(74) *Attorney, Agent, or Firm* — Amster, Rothstein & Ebenstein LLP

(57) ABSTRACT

Protective underwear including a chassis having an absorbent core, a backsheet, and a cover, and gathered elastic side panels attached to the chassis. The protective underwear is made by attaching the side panels along respective edge portions of the chassis while both the chassis and the elastic panels are moving in the machine direction.

2 Claims, 4 Drawing Sheets

LOW RISE PROTECTIVE UNDERWEAR AND METHOD OF FORMING THE SAME

RELATED APPLICATIONS

This application claims priority to and the benefit of U.S. Provisional Application No. 63/134,701, entitled LOW RISE PROTECTIVE UNDERWEAR AND METHOD OF FORMING THE SAME filed Jan. 7, 2021, the contents of which are incorporated herein by reference in their entirety.

FIELD OF THE INVENTION

The present invention generally relates to low rise protective underwear and a method for manufacturing low rise protective underwear.

BACKGROUND

Disposable diapers have been made and sold for many years. Some diapers typically include attachment tabs and are considered bulky and not discreet. Technology and materials have evolved such that protective underwear was developed and has become a growing market. Protective underwear is greatly improved in that attachment tabs are no longer required, and the products tend to be more discreet compared to a diaper. There is a continuing need to provide protective underwear that is less bulky and more discreet.

Protective underwear is generally made by forming an insert/core, moving the insert/core in a machine direction, and then turning the insert/core 90 degrees and applying it to side panels, which typically include elastic materials for stretch-ability. This limits the speed of what a converter can achieve and requires costly equipment to perform the process. Also, in order to form the waist diameter of the product, the side seam panels are bonded together in the middle of the hip area as it relates to end use. This creates an area for discomfort.

There is a continuing need for improved protective underwear and methods for making protective underwear.

SUMMARY OF THE INVENTION

An object of the present invention is to provide a low-rise protective underwear that includes a cover, a backsheet, an absorbent core and side panels, wherein the protective underwear is free from side seam bonds.

In an exemplary embodiment, a method for making protective underwear is provided including forming an absorbent core; placing the absorbent core on a back sheet while moving the absorbent core and backsheet in a machine direction; placing a cover over the absorbent core to form a chassis; feeding elastic panels in the machine direction; and attaching the elastic panels to the chassis.

In an exemplary embodiment portions of the elastic panels are left unattached to the chassis along side edges of the chassis so as to form leg openings.

In an exemplary embodiment the method further comprises attaching hook fasteners to end portions of the elastic panels and attaching the end portions of the elastic panels to the chassis with a partial cut-through.

DETAILED DESCRIPTION OF PREFERRED EMBODIMENTS

Figure 1:
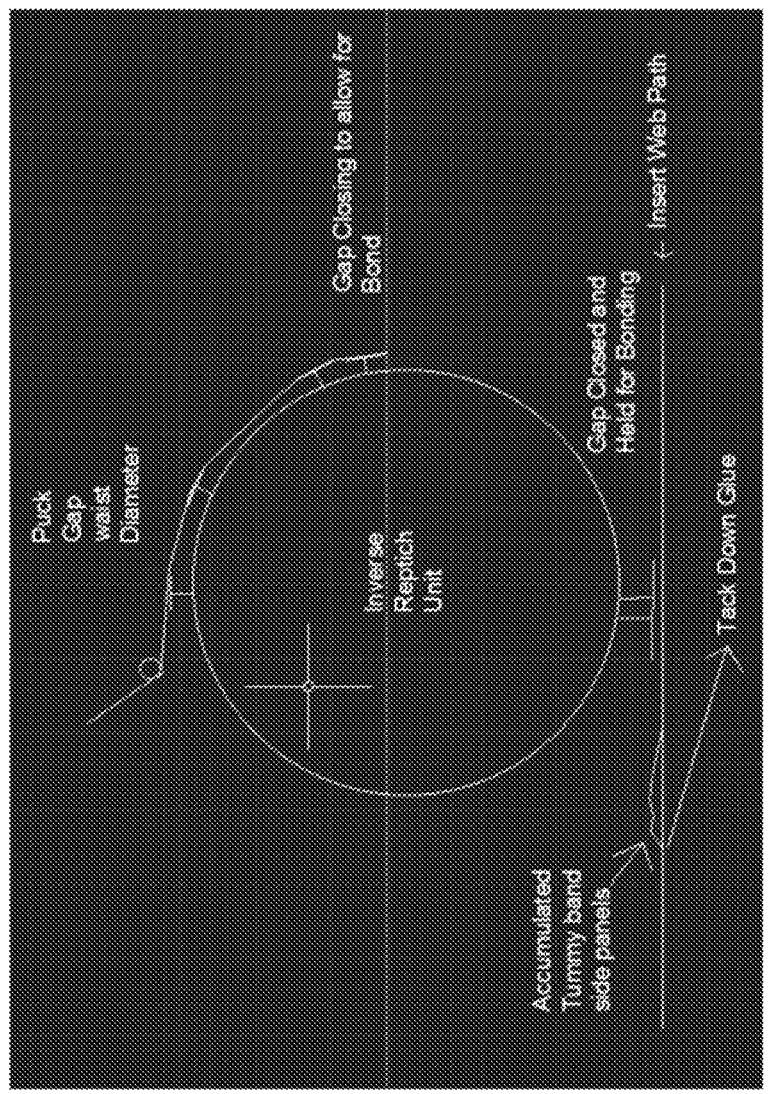
FIG. 1 is a side view of a re-pitch unit according to an exemplary embodiment of the present invention.

Protective underwear according to exemplary embodiments of the present invention include a chassis made up of an absorbent core or insert, a topsheet, a backsheet and elastic side panels.

Absorbent cores or inserts may be formed or cut out from rolls of absorbent materials. As used herein, the term "absorbent core or insert" refers to a material or combination of materials suitable for absorbing, distributing, and storing aqueous fluids such as urine, blood, menses, and water found in body exudates. The size and shape of the absorbent core can be altered to meet absorbent capacity requirements, and to provide comfort to the wearer/user. The absorbent core suitable for use in the present invention can be any liquid absorbent material known in the art for use in absorbent articles, provided that the liquid absorbent material can be configured or constructed to meet absorbent capacity requirements. Nonlimiting examples of liquid absorbent materials suitable for use as the absorbent core include comminuted wood pulp, which is generally referred to as airfelt; creped cellulose wadding; absorbent gelling materials including superabsorbent polymers, such as hydrogel-forming polymeric gelling agents; chemically stiffened, modified, or cross-linked cellulose fibers; meltblown polymers including coform; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof, as is well known in the art of making absorbent products such as sanitary napkins, pantiliners, incontinence pads, and the like.

The core or insert is placed on a top surface of a backsheet. Backsheets are materials that generally are liquid impermeable but may be moisture vapor permeable (breathable). Backsheets are used in absorbent products on a surface of the product that is distal to the user's body. The backsheet can be any known or otherwise effective backsheet material, provided that the backsheet prevents external leakage of exudates absorbed and contained in the protective underwear. Flexible materials suitable for use as the backsheet include, but are not limited to, woven and nonwoven materials, laminated tissue, polymeric films such as thermoplastic films of polyethylene and/or polypropylene, microporous films, composite materials such as a film-coated nonwoven material, or combinations thereof, as is well known in the art of making absorbent products, such as sanitary napkins, pantiliners, incontinence pads, and the like.

The absorbent core or insert is typically attached to the backsheet with an adhesive. Suitable adhesives are known in the art and include hot melt adhesives, emulsion polymer adhesives and the like.

A topsheet or cover is placed on top of the core or insert and attached to the core or insert and backsheet with adhesive, ultrasonic bonding or combinations thereof, forming a chassis. Suitable topsheets are compliant, soft feeling, and non-irritating to the body of the wearer. Suitable topsheet materials include a liquid pervious material that is oriented towards and contacts the body of the wearer, thereby permitting body discharges to rapidly penetrate through the topsheet without allowing fluid to flow back through the topsheet to the skin of the wearer. A suitable topsheet can be made of various materials, such as woven and nonwoven materials; apertured film materials including apertured formed thermoplastic films, apertured plastic films, and fiber-entangled apertured films; hydro-formed thermoplastic films; porous foams; reticulated foams; reticulated thermoplastic films; thermoplastic scrims; or combinations thereof, as is well known in the art of making absorbent products such as sanitary napkins, pantiliners, incontinence pads, protective and the like. The chassis may include additional materials such as acquisition distribution layers, transfer layers, secondary absorbent layers and the like.

Elastic side panels are attached to the chassis to form protective underwear. Any elastic side panel known in the art of absorbent articles may be useful. Suitable elastic side panels include laminates of elastic films with nonwovens, laminates of elastic strands with nonwovens and the like. The elastic panels may be attached to the chassis by adhesive, ultrasonic bonding or a combination thereof. The elastic side panels are attached along side edges of the chassis, which eliminates side seams. The length, width and shape of the side panels may be designed to make protective underwear of different sizes and with different side profiles, such as boxer, low rise or slim. The protective underwear has a more garment like fit and appearance.

In accordance with exemplary embodiments of the present invention, the protective underwear may be made by forming or cutting an absorbent core or insert. The core or insert is placed on a backsheet and fed in a machine direction to a cover placement module, where a cover is attached to the core and backsheet by adhesive, ultrasonic bonding or a combination thereof, forming a chassis. The chassis is fed to an elastic side panel application module where elastic side panels are attached along edges of the chassis by adhesive, ultrasonic bonding or a combination thereof. In embodiments, the elastic side panels are fed in the machine direction, which eliminates the need to turn the chassis in the process of making the protective underwear. This enables a protective underwear manufacturing machine to operate at faster speeds with improved process control.

Figure 2:
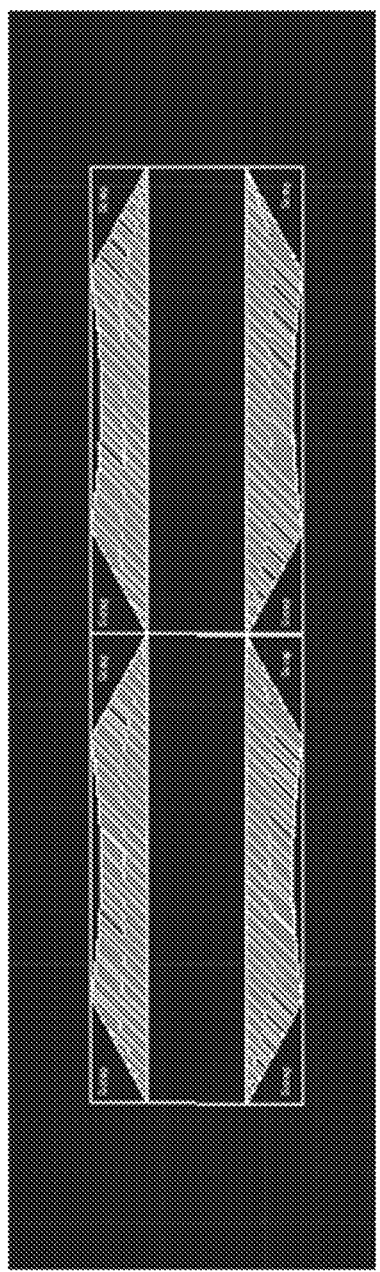
FIG. 2 is a top view of protective underwear during a step of a process for making protective underwear according to an exemplary embodiment of the present invention.
Figure 3:
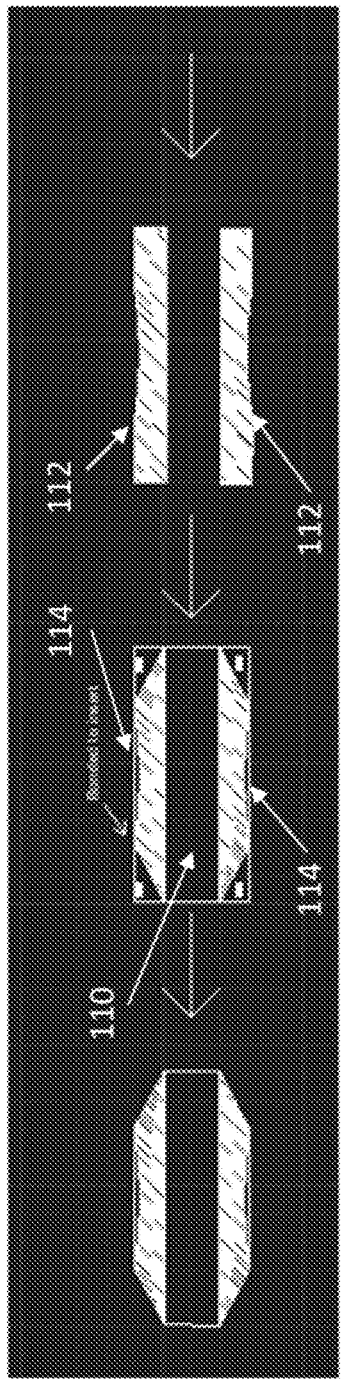
FIG. 3 is a top view of protective underwear during a step of a process for making protective underwear according to an exemplary embodiment of the present invention.
Figure 4:
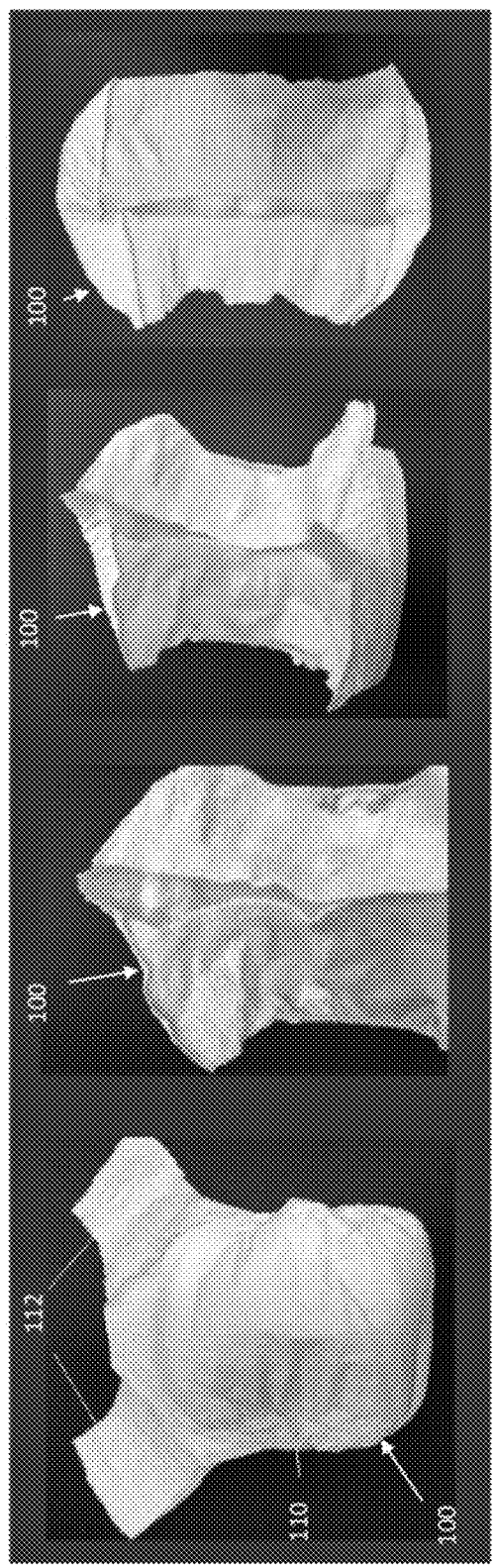
FIGS. 4A, 4B, 4C and 4D are photos of protective underwear according to an exemplary embodiment of the present invention.

FIGS. 2 and 3 show a process for making protective underwear according to an exemplary embodiment of the present invention. As shown in FIG. 3, the method includes moving an absorbent insert/core 110 in a machine direction, where the insert/core 110 has longitudinal side edge portions, a leading-edge portion in the machine direction and a trailing edge portion in the machine direction. Two side panel web paths separated from one another by a predetermined distance are brought down to run parallel to the insert 110. The two side panels 112 are then attached to the insert/core 110, with each side panel 112 attached to the leading and trailing edges portions as well as respective side edge portions of the insert/core 110. In embodiments, the leading and trailing edge portions of the insert/core 110 with the attached side panels 112 form the front and back waist portions (or back and front waist portions), respectively, of the training pant. A portion of each side panel 112 is left unattached to the respective side edge portion of the insert/core 110 to form leg openings 114. The side panels 112 may be attached to the insert/core 110 with glue, adhesive, ultrasonic bonding or combinations thereof. The side panels 112 may be attached to the insert/core 110 at various angles to create a more garment like fit and eliminate the need for side seam bonds. As shown in FIG. 2, a triangle shaped area between product bonds may be cut out and discarded. The bond in turn may face away from the wearer's skin when worn.

FIGS. 4A-4D show protective underwear, generally designated by reference number 100, according to an exemplary embodiment of the present invention. The protective underwear 100 includes a chassis 110 and elastic panels 112 attached to the chassis. As clearly shown in the photos, the protective underwear 100 is devoid of side seams at the hip area of a wearer, which makes for a much more comfortable garment compared to conventional protective underwear.

By varying the side panel widths, several garment styles can be achieved. Examples of styles include, but are not limited to low rise, slim profile, boxer and traditional style briefs. This coupled with a three-piece back sheet design will allow for design of leg cutout features to address varying leg contour profiles.

Side panel web paths may go through a re-pitch unit to allow for additional material longer than the insert/core length to be applied per product. Waist diameters can be modified by adjusting the re-pitch length and not having to add additional costly materials to make the insert/core longer. Some repitch machines include two pucks operating at different speeds which pick up, move and place material on an insert/core. Suitable repitch devices and methods are taught in U.S. Pat. Nos. 9,498,941 and 9,827,147, which are hereby incorporated by reference in their entirety. In prior processes, the product geometry for the waist is dictated by the insert/core length, creating a costly product. The method of the present invention allows over feed side panel webs so a longer side panel may be attached to the same chassis, which enables making a different size waist.

FIG. 1 shows a repitch unit including pucks that retain elastic panels with vacuum and place the elastic panels on absorbent inserts/cores. FIGS. 2 and 3 show the elastic panels moving in the machine direction and placed on the absorbent inserts/cores as the inserts/cores move in the machine direction and attached. A triangle shaped piece of material is cut on each side of the product at distal portions of the product and a transverse cut is made to separate the products.

Figure 5:
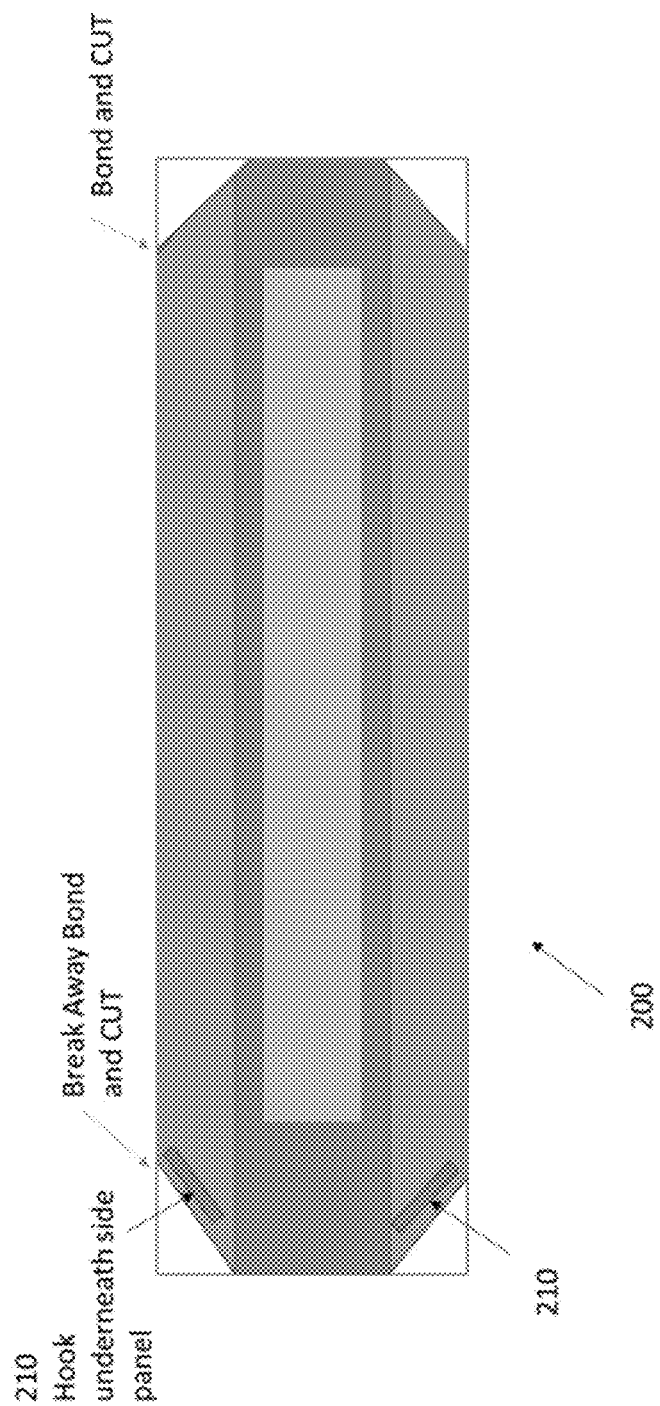
FIG. 5 shows a pull-up recloseable diaper according to an exemplary embodiment of the present invention.

FIG. 5 shows a pull-up recloseable diaper, generally designated by reference number 200, according to an exemplary embodiment of the present invention. The diaper 200 is made using the same process as described with reference to FIGS. 2 and 3, except that hook applicator material in the form of hook fasteners 210 are registered to the product for attachment to end portions of the side panel webs and the end portions of the side panels with the hook fasteners 210 are bonded to the insert with a partial cut-through. The partial cut-through allows a user to pull the end portions of the side panels with the hook material away from the insert, thereby breaking the bonds between those end portions and the insert. The hooks on the underside of the side panels can then be attached to loop material or nonwoven on the underside of the insert chassis. In this regard, the training pant may be "loopless" in that loop elements are not included and instead the hook fasteners directly engage with the insert chassis.

In exemplary embodiments, the hook fasteners 210 may be made up of separate hook elements or may be integral with the side panels. In this regard, the hook elements may be bonded to the side panels by adhesive, ultrasonic, thermal bonding or the like. Alternatively, the hook elements may be intimately joined with the material that forms the side panels. Such intimate bonding of hook elements with a layer of material may be accomplished by feeding extruded plastic and a sheet of material through a nip formed by a first roller having pins and a second roller having corresponding cavities. As the molten plastic is forced through the nip, it flows into the cavities of the second roller and also into pores in the sheet of material. The plastic in the cavities cools and hardens so as to form a hook sheet. At the same time, the sheet of material is intimately joined to and becomes an integral part of the hook sheet so as to form a laminated structure. This process is disclosed in U.S. Pat. No. 5,518,795, the contents of which are incorporated herein by reference in their entirety. The hook elements may be arranged on the side panels in longitudinally extending strips that are laterally spaced from one another. Alternatively, the hook elements may be arranged in a pattern of geometric shapes or lines. Desirably, the hook elements are arranged on an inelastic material in order to improve ease of processing and the shear strength of the seam. Alternatively, hooks may be formed directly into the nonwoven by passing the nonwoven through a nip formed by an ultrasonic horn and rotating hook mold. The nonwoven softens into the mold and is pulled out as the mold rotates.

All processes described above may be run in the machine direction, eliminating the need for insert turning and therefore increasing the machine speed and improving process control.

Now that embodiments of the present invention have been shown and described in detail, various modifications and improvements thereon can become readily apparent to those skilled in the art. Accordingly, the exemplary embodiments of the present invention, as set forth above, are intended to be illustrative, not limiting. The spirit and scope of the present invention is to be construed broadly.

I claim:

1. A method for making protective underwear comprising:
   forming an absorbent core;
   attaching the absorbent core to a backsheet;
   attaching a cover to the core and backsheet to form a chassis;
   moving the chassis in a machine direction on an absorbent product manufacturing machine;
   feeding elastic panels in the machine direction over the chassis; and
   attaching the elastic panels to the chassis to form low rise protective underwear,
   the protective underwear being free of side seam bonds when worn,
   wherein portions of the elastic panels are left unattached to the chassis along side edges of the chassis so as to form leg openings between the chassis and the elastic panels.

2. The method of claim 1, further comprising:
   attaching hook fasteners to end portions of the elastic panels; and
   attaching the end portions of the elastic panels to the chassis with a partial cut-through.

* * * * *